(12) United States Patent
Braun et al.

(10) Patent No.: US 9,365,480 B2
(45) Date of Patent: Jun. 14, 2016

(54) PROCESS FOR THE MANUFACTURE OF ALKENONES

(71) Applicant: SOLVAY SA, Brussels (BE)

(72) Inventors: Max Josef Braun, Wedemark (DE); Stefan Palsherm, Barsinghausen (DE)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 14/422,043

(22) PCT Filed: Aug. 20, 2013

(86) PCT No.: PCT/EP2013/067344
§ 371 (c)(1),
(2) Date: Feb. 17, 2015

(87) PCT Pub. No.: WO2014/029786
PCT Pub. Date: Feb. 27, 2014

(65) Prior Publication Data
US 2015/0239817 A1    Aug. 27, 2015

(30) Foreign Application Priority Data
Aug. 22, 2012  (EP) .................... 12181334

(51) Int. Cl.
C07C 45/65    (2006.01)
C07C 45/82    (2006.01)
C07C 45/41    (2006.01)

(52) U.S. Cl.
CPC ............. *C07C 45/65* (2013.01); *C07C 45/41* (2013.01); *C07C 45/82* (2013.01)

(58) Field of Classification Search
USPC .......................................... 568/391, 394, 398
See application file for complete search history.

(56) References Cited

U.S. PATENT DOCUMENTS

| | | | | |
|---|---|---|---|---|
| 3,285,976 | A * | 11/1966 | Muschelknautz et al. | 568/850 |
| 8,440,865 | B2 * | 5/2013 | Braun et al. | 568/392 |
| 2006/0084813 | A1 | 4/2006 | Hausmann et al. | |
| 2011/0087052 | A1 | 4/2011 | Braun et al. | |
| 2011/0178297 | A1 * | 7/2011 | Braun | 544/315 |
| 2012/0116127 | A1 * | 5/2012 | Braun et al. | 568/391 |
| 2013/0237710 | A1 | 9/2013 | Braun | |

FOREIGN PATENT DOCUMENTS

| | | |
|---|---|---|
| WO | 2004/108647 A2 | 12/2004 |
| WO | 2010/000871 A2 | 1/2010 |
| WO | 2010/037688 A1 | 4/2010 |
| WO | 2011/003860 A1 | 1/2011 |
| WO | 2012/085195 A1 | 6/2012 |

* cited by examiner

*Primary Examiner* — Pancham Bakshi

(57) ABSTRACT

A process for the manufacture of an alkenone comprising the steps of: (a) providing a halogenated precursor of the alkenone and (b) subjecting at least a fraction of the halogenated precursor of step (a) to a thermolysis reaction to form a reaction mixture comprising the alkenone and a hydrogen halide wherein the hydrogen halide is removed from the reaction mixture by cyclonic separation is described.

20 Claims, No Drawings

PROCESS FOR THE MANUFACTURE OF ALKENONES

This application is a U.S. national stage entry under 35 U.S.C. §371 of International Application No. PCT/EP2013/067344 filed Aug. 20, 2013, which claims priority to European application No. 12181334.9 filed 22 Aug. 2012. The entire contents of these applications are explicitly incorporated herein by this reference.

The present invention relates to a process for the manufacture of alkenones.

Halogenated alkenones, such as 4-ethoxy-1,1,1-trifluoro-3-buten-2-one (ETFBO), are building blocks in chemical synthesis, as disclosed, for example, in U.S. Pat. No. 5,708,175. They may be prepared by reacting an acid chloride with a vinyl ether as described in the aforementioned patent, or by reacting an acid anhydride with a vinyl ether.

WO 2011/003860 describes a process comprising a thermolysis of a halogenated precursor of an alkenone. Since the process is carried out in absence of an acid scavenger hydrogen halide is generated in gaseous form and has to be removed from the reaction mixture during or after the reaction e.g. by heating or vacuum.

The present invention now makes available an improved process for the preparation of alkenones, in particular for the preparation of 4-ethoxy-1,1,1-trifluoro-3-buten-2-one (ETFBO).

The process according to the invention allows for a reduction in size of the equipment used in the preparation of the alkenones.

The process according to the invention also allows for a reduction of residence time of the reaction mixture in the reactor or reactors.

The process according to the invention further allows for particularly high selectivity, including configuration isomer selectivity, to the desired alkenone, in particular ETFBO, under productive conditions. The high selectivity allows further for simplified purification and high isolated yield of the target product.

The invention relates to a process for the manufacture of an alkenone comprising the steps of:
(a) providing a halogenated precursor of the alkenone and
(b) subjecting at least a fraction of the halogenated precursor of step (a) to a thermolysis reaction to form a reaction mixture comprising the alkenone and a hydrogen halide wherein the hydrogen halide is removed from the reaction mixture by cyclonic separation.

The term "cyclonic separation" as used herein is intended to denote methods known in the art of separating a gas from a liquid using rotational effects and gravity, including for example centrifugal separation techniques. The cyclonic separation according to the present invention can be performed in a cyclone separator comprising an inlet, for example a tangential inlet, through which the reaction mixture is introduced into a cylindrical cyclone barrel, which may comprise a conical section. Introduction into the barrel imparts a spinning flow pattern to the reaction mixture. The spinning flow pattern may comprise circular, helical, or vortical motion, preferably helical motion. Centrifugal force separates the gaseous components, in particular hydrogen halide, from the liquid components of the reaction mixture. The gaseous components may leave the cyclone barrel through a gas outlet, advantageously an axial gas outlet on the top of the cyclone barrel. The liquid components first travel to the walls of the cyclone barrel and then down along the conical section to a liquid outlet, advantageously in the form of an axial liquid outlet on the bottom of the cyclone barrel. Thus, the gaseous and the liquid components of the reaction mixture are advantageously withdrawn at opposite sides of the cyclone separator.

In a preferred aspect of the invention the process further comprises the steps of (c) transferring the at least a fraction of the reaction mixture from step (b) into a separate reactor, and (d) subjecting the transferred reaction mixture comprising unreacted halogenated precursor to a thermolysis reaction to form further alkenone and hydrogen halide. Advantageously, in this preferred aspect of the invention a fraction of equal to or more than 10% of the hydrogen halide is eliminated from the halogenated precursor of step (a) in step (b), preferably a fraction of equal to or more than 25% of the hydrogen halide is eliminated from the halogenated precursor of step (a) in step (b), more preferably a fraction of equal to or more than 50% of the hydrogen halide is eliminated from the halogenated precursor of step (a) in step (b).

In a further preferred aspect of the invention the process comprises a thermolysis reaction in step (b) and/or in step (d) which is a flash thermolysis reaction.

For the purpose of the present invention, the term "flash thermolysis" refers to a process wherein the liquid reaction mixture is heated up in a short time, preferably less than 20 min, more preferably less than about 15 min. Generally, the heating time is greater than 1 s, often greater than 15 s.

"Heating time" is understood to denote the time required to heat the liquid fraction containing the halogenated precursor, in particular a liquid reaction mixture, from an initial temperature to the temperature of the thermolysis treatment. A typical initial temperature in step (b) is less than 50° C., often less than 40° C., preferably equal to or less than 30° C. In one aspect, the initial temperature is from 15 to 30° C. The initial temperature is generally at least −50° C., often equal to or greater than −40° C., preferably equal to or greater than −30° C. Often, the initial temperature in step (b) corresponds to the temperature of the reaction mixture of step (a) after completion of step (a). A typical initial temperature in step (d) is less than 120° C., often less than 100° C., preferably equal to or less than 90° C. In one aspect, the initial temperature is from 70 to 90° C. The initial temperature is generally at least 20° C., often equal to or greater than 40° C., preferably equal to or greater than 50° C. Often, the initial temperature in step (d) corresponds to the temperature of the reaction mixture of step (c) after completion of step (c).

In step (d), a thermolysis treatment carried out at a temperature of from 90° C. to 120° C., in particular from 95 to 105° C. is particularly preferred. In step (b), a thermolysis treatment carried out at a temperature of from 60° C. to 90° C., in particular from 75 to 85° C. is particularly preferred. It has been found that the aforementioned temperature ranges are particularly efficient, in particular for the thermolysis of 4-chloro-4-ethoxy-1,1,1-trifluoro-butane-3-one (CETFBO) to 4-ethoxy-1,1,1-trifluoro-3-butan-2-one (ETFBO) under elimination of hydrogen chloride. Thus, in a preferred embodiment of the process of the present invention step (b) carried out at a temperature equal to or more than 10° C. lower than the temperature of step (d).

The thermolysis or flash thermolysis may be carried out under vacuum. In that case, the pressure in the reactor is often from 100 to 600 mbar, preferably from 100 mbar to 500 mbar, for example from 200 to 450 mbar. The thermolysis or flash thermolysis can be optionally carried out under stripping with an inert gas stream such as nitrogen gas or argon gas. For the purpose of the present invention, the term "stripping" denotes in particular a physical separation process where one or more components, in particular a hydrogen halide, are removed from the liquid reaction mixture by means of a gas stream. The liquid and gas streams can have concurrent or countercurrent flow directions.

In a preferred embodiment step (a) according to the present is performed in a first reactor and step (b) is performed in a second reactor.

The term "reactor" as used herein is intended to denote a vessel designed to contain chemical reactions. The vessel can for example be a tank reactor, particularly a continuous stirred tank reactor, or a tubular reactor.

The reactor of step (a) is often a tank reactor, preferably a continuously stirred tank reactor. The reactor of step (d) can be, for example, a distillation column.

In a more preferred embodiment, step (b) of the present invention is carried out in a tubular reactor comprising a heating segment. Advantageously, the tubular reactor constitutes part of the piping connecting two reactors such as the piping connecting the reactors of step (a) and step (d). Heating in the heating segment can be carried out by suitable means such as heating the walls of the tubular reactor. Heating can also be solely or in combination with other suitable means carried out by providing a hot gas, in particular a hot inert gas such as in particular nitrogen to the reaction mixture in the heating segment.

The process according to the invention can be performed batch-wise or in a continuous manner. In a preferred embodiment of the invention the process is performed continuously.

In a further preferred embodiment of the invention the halogenated precursor of the alkenone corresponds to Formula (I): $R^1$—C(O)—$CH_2$—CH(X)—$OR^2$ (I) wherein X represents fluorine, chlorine or bromine and $R^1$ represents an alkyl group which is optionally substituted by at least one halogen atom or $R^1$ represents $CF_3C(O)CH_2$; and $R^2$ represents aryl, substituted aryl, or an alkyl group which is optionally substituted by at least one halogen atom. Thus, the process according to the invention can advantageously be applied to the preparation of an alkenone corresponding to the formula $R^1$—C(O)—C(H)=C(H)—$OR^2$. In a more preferred aspect of this embodiment $R^1$ is a fluorinated C1-C4 alkyl group, even more preferably a $CHF_2$, $CClF_2$, or a $CF_3$ group, most preferably a $CF_3$ group. In another preferred aspect $R^2$ is a C1-C4 alkyl group, preferably a methyl or an ethyl group. Particularly, the alkenone the process according to the invention is applied to the preparation of 4-ethoxy-1,1,1-trifluoro-3-butan-2-one.

The term "alkyl group" is intended to denote saturated hydrocarbon-based groups, such as, in particular, a C1-C6 alkyl group. By way of example, mention may be made of methyl, ethyl, propyl, isopropyl, butyl, t-butyl, pentyl, isopentyl and hexyl.

The term "aryl group" is intended to denote a group which is derived from an aromatic nucleus such as a C6-C10 aromatic nucleus, in particular a phenyl or naphthyl nucleus.

The hydrogen halide removed from the reaction mixture can be for example hydrogen bromide, hydrogen chloride or hydrogen fluoride. In a preferred embodiment of the invention the hydrogen halide is hydrogen chloride.

Step (a) of the process according to the invention comprises providing a halogenated precursor of the alkenone. This can be carried out for example by filling or pumping the halogenated precursor into a reactor. The halogenated precursor may be supplied for example by transportation of previously produced halogenated precursor in a suitable tank. However, it is preferably provided by reaction of starting compounds which themselves are suitable precursors of the halogenated precursor such as acid chlorides or acid anhydrides and vinyl ether.

Advantageous embodiments in particular for manufacture of 4-chloro-4-ethoxy-1,1,1-trifluoro-butane-3-one (CETFBO) from ethyl vinylether (EVE) and trifluoroacetylchloride (TFAC) are selected from (1) carrying out the reaction in a reaction mixture containing carboxylic acid halide, (2) carrying out the reaction in a reaction mixture using alkenone and/or halogenated precursor as solvent, (3) carrying out the reaction under conditions allowing to avoid or minimize hot spots, in particular by carrying out the reaction in a turbulent state, (4) carrying out the reaction in the absence of an acid scavenger for hydrogen halide and combinations of these embodiments. These embodiments are explained in further detail in WO 2010/000871, WO 2011/003854, WO 2011/003856 and WO 2004/108647, respectively, the contents of which is incorporated by reference into the present patent application.

Another preferred embodiment of the invention is a process comprising at least one further step (e) comprising conversion of the alkenone to a heterocyclic compound wherein the hydrogen halide formed in step (b) and/or step (d) is used in step (e). Preferably, the heterocyclic compound is a $CF_3$-pyridine derivative or a $CF_3$-pyrazole derivative.

The term "hydrogen halide formed in step (b) and/or step (d) is used in step (e)" as used in this embodiment is intended to denote use of the hydrogen halide for example as a catalyst for the conversion of the alkenone to the heterocyclic compound in step (e) or use of the hydrogen halide for the formation of a hydrogen halide salt of any component of the reaction mixture of step (e), particularly for the formation of a hydrogen chloride salt of the $CF_3$-pyridine derivative of step (e).

It has been found that the process of the present invention allows for a reduction in size of the reactors used for the manufacture of the alkenone. The reduction in reactor size provides the possibility of a reduced residence time, i.e. the time the reaction mixture spends in the reactor from entering to exiting it. It has been found that side reactions are dramatically reduced using the process of the present invention as compared to the processes of the prior art. One side reaction is the Hetero-Diels-Alder reaction of two molecules of the alkenone, especially when ETFBO is prepared.

Another side reaction is the addition of the hydrogen halide to the alkenone leading to the formation of the halogenated precursor and/or to the formation of oligomers and polymers of the alkenone. It has been found that the addition of hydrogen halide to the alkenone, i.e. the reversal of the reaction of step (b), is minimised using the process of the present invention.

Should the disclosure of any patents, patent applications, and publications which are incorporated herein by reference conflict with the description of the present application to the extent that it may render a term unclear, the present description shall take precedence.

EXAMPLES

Continuous Preparation of
4-ethoxy-1,1,1-trifluoro-3-buten-2-one

Pure 4-ethoxy-1,1,1-trifluoro-3-buten-2-one (ETFBO), obtained by a previous synthesis, is placed in the flow part of a recirculation system and cooled using a chiller. This recirculation system comprises a 20 L flask, 2 one meter distillation columns filled with 10 mm glass Raschig rings placed on top of another distillation column, a circulation pump (1500 l/h), 3 tube reactors each with 3 m path length (diameter 1.5 cm). Once the desired temperature is reached in the recirculation system, gaseous or liquid trifluoroacetylchloride (15 kg/h; 113.2 mol/h) is introduced into the turbulent circulation in front of the first 3 m reactor and then a small molar excess of ethyl vinyl ether (TFAC/EVE=1:1.01) is added after the first 3 m reactor. The level of reaction mixture in the 20 L flask of the recycle apparatus is kept constant by pumping material using a membrane pump into a pipe connected to a cyclone separator. The pipe is heated by means of a heating mantle to a temperature of 80° C. The hydrogen chloride formed in this step is removed from the reaction mixture through the gas outlet of the cyclone separator. The liquid material is transferred through liquid outlet of the cyclonic separator and further pumped into an reactor for the second thermolysis of 4-chloro-4-ethoxy-1,1,1-trifluoro-3-butan-2-one (CETFBO) to 4-ethoxy-1,1,1-trifluoro-3-buten-2-one (ETFBO). The apparatus comprises a 100 L Pfaudler ceramic vessel operated at a temperature of 100° C. with 3 one meter distillation columns filled with 10 mm glass Raschig rings and a cooler with removal. The further conversion of CETFBO to ETFBO under loss of hydrogen chloride takes place through continuous feeding of the liquid reaction mixture from the cyclone in the distillation columns. The crude product thus obtained can optionally be further purified by fine distillation.

The invention claimed is:

1. A process for the manufacture of an alkenone comprising the following steps:
   (a) providing a halogenated precursor of the alkenone and
   (b) subjecting at least a fraction of the halogenated precursor of step (a) to a thermolysis reaction to form a reaction mixture comprising the alkenone and a hydrogen halide wherein the hydrogen halide is removed from the reaction mixture by cyclonic separation.

2. The process of claim 1 further comprising the steps of
   (c) transferring at least a fraction of the reaction mixture from step (b) into a separate reactor, and
   (d) subjecting the transferred reaction mixture comprising unreacted halogenated precursor to a thermolysis reaction to form further alkenone and hydrogen halide.

3. The process of claim 2 wherein a fraction of equal to or more than 10% of the hydrogen halide is eliminated from the halogenated precursor of step (a) in step (b).

4. The process of claim 1 wherein the thermolysis reaction in step (b) is a flash thermolysis reaction.

5. The process of claim 2 wherein step (b) is carried out at a temperature equal to or more than 10° C. lower than the temperature of step (d).

6. The process of claim 1 wherein step (a) is performed in a first reactor and step (b) is performed in a second reactor.

7. The process of claim 6 wherein the reactor in step (b) is a tubular reactor comprising a heating segment.

8. The process of claim 1 wherein the process is performed continuously.

9. The process of claim 1, wherein the halogenated precursor of the alkenone corresponds to Formula (I): $R^1$—C(O)—$CH_2$—CH(X)—$OR^2$ (I) wherein X represents fluorine, chlorine or bromine and $R^1$ represents an alkyl group which is optionally substituted by at least one halogen atom or $R^1$ represents $CF_3C(O)CH_2$; and $R^2$ represents aryl, substituted aryl, or an alkyl group which is optionally substituted by at least one halogen atom.

10. The process of claim 9, wherein $R^1$ is a fluorinated C1-C4 alkyl group.

11. The process of claim 9, wherein $R^2$ is a C1-C4 alkyl group.

12. The process of claim 1 wherein the alkenone is 4 ethoxy-1,1,1-trifluoro-3-buten-2-one.

13. The process of claim 1 wherein the hydrogen halide is hydrogen chloride.

14. The process according to claim 1 comprising at least one further step (e) comprising conversion of the alkenone to a heterocyclic compound wherein the hydrogen halide formed in step (b) is used in step (e).

15. The process according to claim 14 wherein the heterocyclic compound is a $CF_3$-pyridine derivative or a $CF_3$-pyrazole derivative.

16. The process of claim 2 wherein the thermolysis reaction in step (b) and/or in step (d) is a flash thermolysis reaction.

17. The process of claim 10, wherein $R^1$ is a $CHF_2$, $CClCF_2$, or a $CF_3$ group.

18. The process of claim 17, wherein $R^1$ is a $CF_3$ group.

19. The process of claim 11, wherein $R^2$ is a methyl or an ethyl group.

20. The process according to claim 2 comprising at least one further step (e) comprising conversion of the alkenone to a heterocyclic compound wherein the hydrogen halide formed in step (b) and/or step (d) is used in step (e).

* * * * *